| United States Patent [19] | [11] | 4,221,810 |
|---|---|---|
| Tahara et al. | [45] | Sep. 9, 1980 |

[54] ANTIULCER COMPOUNDS

[75] Inventors: Yoshiyuki Tahara, Oi; Michiko Nagai, Wako; Katsura Kogure, Kawagoe; Shigeo Kawase, Tsurugashima; Teruhito Yamaguchi, Tokyo, all of Japan

[73] Assignee: Nisshin Flour Milling Co., Ltd., Tokyo, Japan

[21] Appl. No.: 889,568

[22] Filed: Mar. 23, 1978

[51] Int. Cl.² ............... A61K 31/355; C07D 311/72

[52] U.S. Cl. .................. 424/284; 260/345.5; 260/410.9 R; 260/413; 424/312; 424/314; 424/318

[58] Field of Search .............. 260/345.5; 424/284

[56] References Cited

U.S. PATENT DOCUMENTS

| 3,878,202 | 4/1975 | Fukawa et al. | 260/345.5 |
| 4,039,559 | 8/1977 | Nakamura | 260/345.5 |

Primary Examiner—Nicky Chan
Attorney, Agent, or Firm—Haseltine, Lake & Waters

[57] ABSTRACT

α-Tocopheryl derivatives, useful as agents for the treatment of ulcer, are described.

2 Claims, No Drawings

ANTIULCER COMPOUNDS

The present invention relates to an antiulcer agent comprising a compound represented by the general formula

R—Z wherein R means a saturated or unsaturated aliphatic group which may possess a hydroxyl group or an epoxy ring as substituent, and Z means COOR' (wherein R' means hydrogen atom, or alkyl group, phytyl group, isophytyl group, dihydrophytyl group, decaprenyl group or solanesyl group) or hydroxyl group, as its effective component.

A good number of compounds having antiulcer activity such as gefarnate (*Gefanil*, Trade name of Sumitomo Chemical Co. Ltd. for 3,7-dimethyl-2,6-octadienyl-5,9,13-trimethyl-4,8,12-tetradecatrienoate) and the like have been proposed for the treatment of peptic ulcer. However, no compounds so far reported possess satisfactory preventive and curative effects for peptic ulcer. As the results of extensive studies in this field, we have found a group of compounds which are very effective for the therapy of peptic ulcer.

The compounds of this invention, represented by the general formula (I) may be prepared, for instance, according to the process described below.

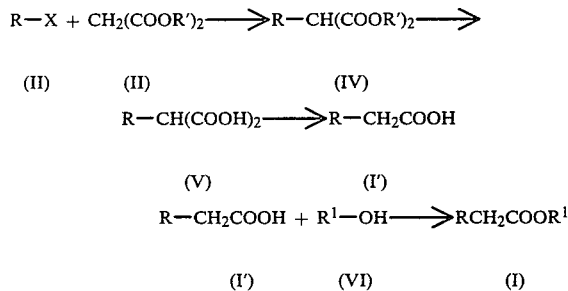

In the above formulae, R means a saturated or unsaturated aliphatic group, which may have a hydroxyl group or an epoxy ring as substituent, X means a halogen atom, R' means a lower alkyl group and $R^1$ means an alkyl, phytyl, isophytyl, dihydrophytyl, decaprenyl or solanesyl group or α-tocopherol residue. Decaprenyl group is 3, 7, 11, 15, 19, 23, 27, 31, 35, 39-decamethyl-2,6,10,14,18,22,26,30,34,38-tetracontadecaenyl group.

First, an aliphatic halide represented by the general formula (II) is condensed with a di-lower alkyl malonate ester represented by the general formula (III) in an alcohol in the presence of an alkali metal alcoholate to produce a di-lower alkyl aliphatic malonate ester having the general formula (IV). The alcohol which is used for this reaction may include methanol, ethanol, isopropanol, t-butanol and the like, and the alkali metal which is used may include sodium, potassium and the like. The reaction temperature is in the range of 60°–100° C., with about 80° C. being preferable. The reaction period is preferably in the range of 2–10 hours, but normally the reaction is almost complete in about 5 hours.

Then the di-lower alkyl aliphatic malonate ester represented by the general formula (IV) is hydrolysed with an alkali in an alcohol, and then neutralized with an acid to produce an aliphatic malonic acid having the general formula (V). The alcohol which may be used in the reaction may include metanol, ethanol and isopropanol, and the alkali which is used may include sodium hydroxide, potassium hydroxide and the like. The reaction is suitably carried out at 75°–85° C. for 3–5 hours. The resulting aliphatic malonic acid of the general formula (V) is then heated under reduced pressure to effect decarboxylation to yield an acetic acid derivative represented by the general formula (I'). Of course, some of such acetic acid derivatives, e.g. oleic acid, stearic acid, etc., are readily available under the market.

To obtain ester derivatives of those compounds, the acetic acid derivative represented by the above general formula (I') is condensed with an alcohol represented by the general formula (VI) to form an alkyl ester of the acetic acid derivative with the general formula (I). The ester formation may be effected by any of the known methods such as acid chloride method, acid anhydride method, direct esterification, substitution method, ester exchange reaction, diazoalkyl method and the like. However, to avoid side reactions being involved, the reaction conditions should desirably be kept as mild as possible. For example, when acid chloride method is adopted, an acetic acid derivative of the general formula (I') or a salt thereof is dissolved or dispersed in a solvent such as benzene, toluene and the like, and with cooling and stirring, an halogenating agent such as oxalyl chloride, thionyl chloride or phosphorus pentachloride is slowly added thereto. After agitating the mixture at room temperature for further 1–6 hours, followed by heating, if required, an acid halide is produced. Then the resulting acid halide is reacted with an alcohol without any solvent or in the presence of an inert solvent such as benzene, toluene, xylene and the like, and in the presence of a base to produce an ester. The base which may be used in the reaction may include a tertiary organic base such as pyridine, quinoline, triethylamine, N,N-dimethylaniline, alkali or alkaline earth metal carbonate such as sodium carbonate, potassium carbonate, sodium bicarbonate, calcium carbonate, or alkali or alkaline earth metal hydroxide such as sodium hydroxide, potassium hydroxide and the like. However, a tertiary organic base such as pyridine and the like is preferred. The reaction is normally effected at 0°–80° C. for 1–5 hours. After completion of the reaction, the reaction mixture is poured into water and extracted in a usual manner with an organic solvent such as ethyl ether. The extract is washed sequentially with water, dilute hydrochloric acid, aqueous sodium bicarbonate solution and saturated aqueous sodium chloride solution, and dried. Removal of the solvent by evaporation under reduced pressure yields an alkyl ester of the present invention.

When the esterification is to be effected by substitution reaction, for example, an alkali metal salt, a silver salt or a tertiary organic base salt such as triethylamine salt of an acetic acid derivative (I') is reacted with an alkyl halide or a sulfate or sulfonate ester of an alcohol to produce an alkyl ester in its highly purified state. As a solvent used in the reaction, a polar solvent such as N,N-dimethylformamide, N,N-dimethylacetamide, dimethylsulfoxide, hexamethyl phosphoric triamide and the like are especially preferable. The reaction is suitably carried out at room temperature to 120° C. for 2–24 hours. After completion of the reaction, the reaction mixture is processed in a similar manner, as described above for the esterification by acid chloride method, to produce an alkyl ester of the present invention.

The acetic acid derivatives of the present invention obtained by the process described above may, if required, by subjected to further purification by vacuum distillation or column chromatography and the like.

The physiological activity of the active compounds according to the present invention will be shown below.

In the case of reserpine-induced ulcer, the assay was performed according to the description in "Arch. Int. Pharmacodym. Ther. 147,113 (1964)", and in the case of acetic acid-induced ulcer, the assay was performed according to the method described in "Jap. J. Pharmac. 19,418 (1969)", by inducing experimental ulcer in rat and evaluating the effect thereon of the compounds tested.

I. Reserpine-induced ulcer (Preventive test)

Groups of rats, each consisting of 6 male SD rats weighing 150–200 g were used. After 24 hours' fasting, a sample compound was orally administered to the rat at the dose of 100 mg/kg body weight, and 30 minutes after the administration, reserpine was intraperitoneally injected at the dose of 15 mg/kg body weight. Eighteen hours after the administration, the rats were killed with chloroform. The stomach was taken out, and severity of the hermorrhaging lesion was evaluated according to the method as above ("Arch. Int. Pharmacodym. Ther." 147,113 (1964)).

The preventive ratio was calculated using the following equation, $$\text{Preventive Ratio} = \frac{\text{Control (Ulcer Index)} - \text{Test (Ulcer Index)}}{\text{Control (Ulcer Index)}} \times 100,$$

wherein the control animals were intraperitoneally given reserpine only, at the dose of 15 mg/kg body weight.

The results are given in Table 1, using the following signs.

| Preventive Ratio | Sign |
|---|---|
| –10% | ± |
| 10%–40% | + |
| 40%–60% | ++ |
| 60%– | +++ |

II. Acetic acid-induced ulcer (Curative test)

Groups of rats, each consisting of 6 male SD rats weighing 150–200 g were used. The stomach of ether-anesthesized rat was exposed and while taking acre not to injure blood vessels, 0.05 ml of 15% aqueous acetic acid solution was injected underneath the serosa. On the 14th day, the rats were killed with chloroform, the stomach taken out and the area of the infected lesion measured.

The curvative ratio was calculated using the above equation:

$$\text{Curative Ratio} = \frac{\text{Control (area)} - \text{Test (area)}}{\text{Control (area)}} \times 100$$

The results are shown in Table 2, using the following signs:

| Curative Ratio | Sign |
|---|---|
| –10% | ± |
| 10%–25% | + |
| 25%–40% | ++ |
| 40%– | +++ |

Table 1

| Compounds | Preventive effect | $LD_{50}(g/kg)$ |
|---|---|---|
| Phytylacetic acid | + | >5 |
| Methyl phytylacetate | + | >5 |
| Decaprenylacetic acid | ++ | >4 |
| Isopropyl phytylacetate | + | >5 |
| Phytyl acetate | ++ | >5 |
| Phytyl geranylacetate | + | >5 |
| Phytyl citronellylacetate | + | >5 |
| Phytyl farnesylacetate | + | >5 |
| Phytyl laurate | ++ | >5 |
| Phytyl palmitate | ++ | >5 |
| Phytyl oleate | +++ | >4 |
| Isophytyl oleate | +++ | >4 |
| Phytyl phytylacetate | ++ | >5 |
| Phytyl phytylacetate | ++ | >4 |
| Phytyl erucate | + | >4 |
| Phytyl brassidate | + | >4 |
| Phytyl decaprenylacetate | + | >4 |
| Dihydrophytyl stearate | + | >4 |
| Dihydrophytyl oleate | + | >4 |
| Solanesyl acetate | ++ | >4 |
| Solanesyl farnesylacetate | + | >4 |
| Solanesyl oleate | + | >4 |
| Solanesyl phytylacetate | + | >4 |
| Solanesyl solanesylacetate | + | >4 |
| Solanesyl decaprenylacetate | + | >4 |
| Decaprenyl acetate | ++ | >5 |
| Decaprenyl elaidate | + | >5 |
| Decaprenyl oleate | ++ | >5 |
| Decaprenyl phytylacetate | ++ | >5 |
| α-Tocopheryl geranylacetate | ++ | >4 |
| α-Tocopheryl citronellylacetate | +++ | >4 |
| α-Tocopheryl farnesylacetate | ++ | >4 |
| α-Tocopheryl phytylacetate | + | >4 |
| α-Tocopheryl solanesylacetate | ++ | >4 |
| α-Tocopheryl decaprenylacetate | + | >4 |
| Solanesol | + | >4 |
| Isodecaprenol | + | >4 |
| Saturated decaprenol | + | >5 |
| Gefarnate (control) | + | |

Table 2

| Compounds | Curative effect | $LD_{50}(g/kg)$ |
|---|---|---|
| Phtylacetic acid | + | >5 |
| Solanesylacetic acid | + | >4 |
| Methyl solanesylacetate | ++ | >4 |
| Ethyl solanesylacetate | ++ | >4 |
| Decaprenylacetic acid | +++ | >4 |
| Methyl decaprenylacetate | ++ | >4 |
| Ethyl decaprenylacetate | +++ | >4 |
| Isopropyl decaprenylacetate | + | >4 |
| Isoamyl decaprenylacetate | + | >4 |
| Phytyl acetate | + | >5 |
| Phytyl stearate | + | >4 |
| Phytyl oleate | +++ | >4 |
| Isophytyl oleate | +++ | >4 |
| Phytyl elaidate | + | >4 |
| Phytyl linoleate | + | >4 |
| Phytyl petroselinate | ++ | >5 |
| Phytyl ricinoleate | + | >5 |
| Phytyl 9,10-epoxystearate | + | >5 |
| Phytyl brassidate | ++ | >4 |
| Phytyl decaprenylacetate | + | >4 |
| Solanesyl geranylacetate | + | >4 |
| Solanesyl oleate | ++ | >4 |
| Decaprenyl acetate | + | >5 |
| Decaprenyl geranylacetate | + | >5 |
| Decaprenyl farnsylacetate | ° | >5 |

Table 2-continued

| Compounds | Curative effect | LD$_{50}$(g/kg) |
|---|---|---|
| Decaprenyl oleate | ++ | >5 |
| Decaprenyl petroselinate | ++ | >4 |
| Decaprenyl brassidate | ++ | >4 |
| Decaprenyl phytylacetate | ++ | >5 |
| Decaprenyl solabesylacetate | + | >5 |
| Decaprenyl decaprenylacetate | + | >5 |
| α-Tocopheryl geranylacetate | + | >4 |
| α-Tocopheryl farnsylacetate | ++ | >4 |
| α-Tocopheryl phytylacetate | +++ | >4 |
| Solanesol | ++ | >4 |
| Decaprenol | +++ | >4 |
| Isodecaprenol | ++ | >4 |
| Saturated decaprenol | ++ | >5 |
| Gefarnate (Control) | ± | |

The results given above clearly show that the active compounds according to the present invention possess excellent antiulcer activity. Moreover, the compounds of the present invention possess therapeutic effect not only on reserpine- or acetic acid-induced ulcer but also on ulcers of various other types. As shown in Tables 1 and 2, the acute toxicity of the present compounds is quite low, when examined by intraperitoneal route in mice. The active compounds of the present invention may be administered intravenously, subcutaneously, intramuscularly or orally. Oral and intramuscular administration is preferred. The dosage of the present active compounds used for the treatment of a human adult is in the range of 100-1000 mg per day, with the range of 200-300 mg per day being preferable.

For oral administration, the present active compounds may take the form of tablet, granules or powder; if required the granules or powder may be formulated as capsules and used in the form of dosage unit. Those solid preparations for oral administration may contain any ordinary excipient such as anhydrous silicic acid, magnesium metasilicate aluminate, synthetic aluminum silicate, lactose, sucrose, corn starch, microcrystalline cellulose, hydroxypropyl starch or glycine, binding agent such as gum arabic, gelatin, tragacanth, hydroxypropyl cellulose or polyvinyl pyrrolidone, lubricant such as magnesium stearate, talc or silica, disintegrating agent such as potato starch or carboxymethylcellulose calcium salt, or wetting agent such as polyethyleneglycol, sorbitan monooleate, polyoxyethylene-hardened castor oil, sodium laurylsulfate. The tablets may be coated in a usual manner.

Liquid preparations for oral administration may take the form of aqueous or oil emulsion or syrup, or dry powder preparation which may be redissolved in a suitable vehicle before use. Those liquid preparations may contain usual additives such as emulsifying aid, e.g. sugar syrup, methycellulose, gelatin, hydroxyethylcellulose, emulsifying agent e.g. lecithin, sorbitan monooleate, polyoxyethylene-hardened castor oil, nonaqueous vehicle e.g. fractionated coconut oil, almond oil, arachis oil, or antiseptic agent e.g. methyl p-hydroxybenzoate, propyl p-hydroxybenzoate or sorbic acid. Those preparations for oral administration may, if required, contain preservatives, stabilizing agents and the like.

When the compounds are to be administered by injection, their preparations may take the form of oil solution, emulsion, aqueous solution and the like. Those solvent may contain usual emulsifying agent, stabilizing agent and the like.

Those pharmaceutical compositions may contain more than 1%, preferably 5-50%, of the present compounds, depending on the route of administration.

The followings are the examples of the synthesis of the compounds and of their pharmaceutical preparations, but they are not intended to limit the scope of the present invention.

EXAMPLE 1

Decaprenylacetic acid

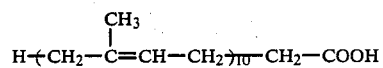

Sodium metal (3.0 g) was dissolved in 200 ml of absolute ethanol and 25.0 g of diethyl malonate was added thereto. Then, under reflux, at 75°-82° C., 100 g of decaprenyl bromide was added dropwise over 4 hours. After further stirring at 75°-82° C. for one hour, the reaction mixture was poured into water and extracted with ethyl acetate. The ethyl acetate extract was sequentially washed with water and saturated sodium chloride solution, and then dried over anhydrous magnesium sulfate. After evaporating off the ethyl acetate under reduced pressure the resultant oily residue weighing 111.2 g was, with the addition of 26.1 g of potassium hydroxide in 500 ml of ethanol, heated at 78°-80° C. for 3.0 hours in nitrogen atmosphere. After cooling, the reaction mixture was acidified to pH 3.0 with concentrated hydrochloric acid and extracted with ether. The ether extract was sequentially washed with water and saturated sodium chloride solution, and dried over magnesium sulfate. The ether was evaporated off under reduced pressure and the resulting concentrate (89.0 g) was heated at 150° C. under reduced pressure (1-10 mm Hg) for 3 hours to complete decarboxylation. Purification through silica gel column chromatography gave 27.4 g of semicrystalline decaprenylacetic acid.

IR $\nu_{max}$ cm$^{-1}$: 2800-2400 (COOH), 1710 (C=O), 1665 (C=C), 840.

NMR $\delta_{TMS}^{CDCl_3}$:

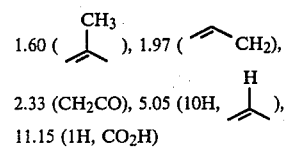

2.33 (CH$_2$CO), 5.05 (10H, ⊥), 11.15 (1H, CO$_2$H)

Elementary analysis: Calculated for C$_{52}$H$_{84}$O$_2$: C, 84.26; H, 11.42(%). Found: C, 84.47; H, 11.27(%).

Solanesylacetic acid was prepared in a similar manner as that described in Example 1. The physical constants are given below.

Solanesylacetic acid

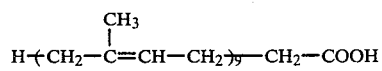

IR$\nu_{max}$cm$^{-1}$: 2800-2400 (COOH), 1710 (C=O), 1665 (C=C), 840.

NMR $\delta_{TMS}^{CDCl_3}$:

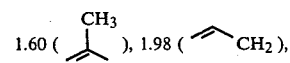

-continued 2.33 (CH₂CO), 5.05 (9H, 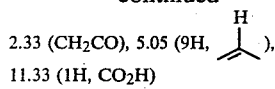),
11.33 (1H, CO₂H)

Elementary analysis: Calculated for $C_{47}H_{76}O_2$: C, 83.87; H, 11.38(%). Found: C, 84.25; H, 11.18(%).

EXAMPLE 2

Ethyl decaprenylacetate

Sodium metal (0.46 g) was dissolved in 200 ml of absolute ethanol, and 122 g of decaprenylacetic acid was added thereto. After stirring for some time, the ethanol was evaporated under reduced pressure. To a dispersion of the residue in 160 ml of dry benzene, 10 ml of oxalylchloride was added over about 15 minutes, under ice cooling and with stirring, and the mixture was further stirred for two hours at room temperature. After concentration of the reaction mixture under reduced pressure, 200 ml of dry ethylene chloride was added thereto. The soluble fraction was added dropwise over about 15 minutes to an ice-cooled and stirred solution of 5 ml of ethanol in 100 ml of dry ethylene chloride and 6 ml of pyridine. The resulting solution was further stirred for 2 hours at room temperature. The reaction mixture was poured into 200 ml of stirred ice water and extracted with ether. The ether extract was sequentially washed with water, dilute hydrochloric acid, saturated sodium bicarbonate solution and saturated sodium chloride solution and then the solvent was evaporated under reduced pressure. The residue was purified by means of silica gel column chromatography to give 8.7 g of ethyl decaprenylacetate as colourless oil.

IR$\nu_{max}$ cm$^{-1}$: 1740 (C=O), 1670 (C=C).

NMR $\delta_{TMS}^{CDCl_3}$:

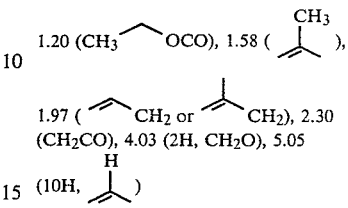

1.20 (CH₃⌒OCO), 1.58 ( ), 1.97 (⌒CH₂ or ⌒CH₂), 2.30 (CH₂CO), 4.03 (2H, CH₂O), 5.05 (10H, )

Elementary analysis: Calculated for $C_{54}H_{88}O_2$: C, 84.31; H, 11.53(%). Found: C, 84.60; H, 11.34(%).

The following compounds were prepared in an analogous manner. The results of elementary analysis and nuclear magnetic resonance spectrum measurements of those compounds are shown in Tables 3 and 4 respectively.

Table 3

| Compound No. | Compounds | Empirical formula | Elementary analysis (%) | | | |
|---|---|---|---|---|---|---|
| | | | Calculated | | Found | |
| | | | C | H | C | H |
| 1 | Methyl solanesylacetate | $C_{48}H_{78}O_2$ | 83.90 | 11.44 | 84.02 | 11.49 |
| 2 | Ethyl solanesylacetate | $C_{49}H_{80}O_2$ | 83.94 | 11.50 | 83.88 | 11.63 |
| 3 | Methyl decaprenylacetate | $C_{53}H_{86}O_2$ | 84.29 | 11.48 | 84.46 | 11.57 |
| 4 | Isopropyl decaprenylacetate | $C_{55}H_{90}O_2$ | 84.33 | 11.58 | 84.35 | 11.51 |
| 5 | Isoamyl decaprenylacetate | $C_{57}H_{94}O_2$ | 84.27 | 11.79 | 83.91 | 11.50 |
| 6 | Methyl phytylacetate | $C_{23}H_{44}O_2$ | 78.34 | 12.58 | 78.41 | 12.62 |
| 7 | Isopropyl phytylacetate | $C_{25}H_{48}O_2$ | 78.88 | 12.71 | 78.82 | 12.63 |

Table 4

δ values (CDCl₃ solution, TMS, 60 MHz)

| Compounds No. | CH₃⌃ | CH₃⌃ | ⌃CH₂/CH₂ | CH₂CO | CH₂O | H⌃ | Remarks |
|---|---|---|---|---|---|---|---|
| 1 | — | 1.60 | 2.00 | 2.30 | — | 5.10(9H) | 3.65(3H, CH₃OCO) |
| 2 | — | " | " | " | 4.10(2H) | 5.10(9H) | 1.24(3H, CH₃⌒OCO) |
| 3 | — | " | " | " | — | 5.05(10H) | 3.60(3H, CH₃OCO) |
| 4 | 1.2 | " | " | " | — | 5.10(10H) | 5.10(1H, OCH⟨) |
| 5 | 0.93 | " | " | " | 4.05(2H) | 5.07(10H) | — |
| 6 | 0.87 | " | " | " | — | 5.05(1H) | 3.63(3H, CH₃OCO) |
| 7 | 0.87, 1.22 | " | 1.95 | " | — | 5.05(1H) | 5.05(1H, O—CH⟨) |

The numbers in the column under "Compounds" correspond to the respective compound numbers in Table 3.

EXAMPLE 3

Phytyl oleate and isophytyl oleate

Phytyl oleate

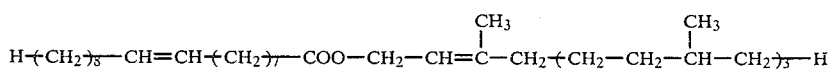

Isophytyl oleate

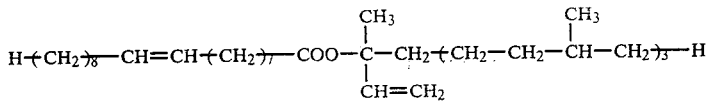

A mixture of 15 g of phytol, 11 g of dicyclohexylcarbodiimide and 0.1 g of cuprous chloride was stirred at 90°-100° C. for two hours under nitrogen, to which 16 g of oleic acid was added, followed by further two hours' stirring at 90°-100° C. After cooling, the reaction mixture was added with 100 ml of n-hexane, freed from any insoluble matters through filtration and the filtrate was concentrated under reduced pressure. The residue was subjected to silica gel chromatography to yield 12.6 g of isophytyl oleate from the first eluting fraction and 5.9 g of phytyl oleate from the later eluting fraction.

Physical constants for phytyl oleate are as follows
IR$\nu_{max}$ cm$^{-}$: 1730 (C=O), 1670 (C=C), 970.
NMR $\delta_{TMS}^{CDCl_3}$:

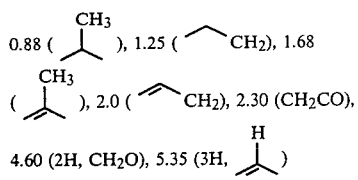

Elementary analysis: Calculated for $C_{38}H_{72}O_2$: C, 81.36; H, 12.94(%). Found: C, 81.49; H, 13.08(%).

Physical constants for isophytyl oleate are as follows.
IR$\nu_{max}$ cm$^{-}$: 3100 (=CH$_2$), 1730 (C=O), 1640 (C=C), 995, 925.
NMR $\delta_{TMS}^{CCl_4}$:

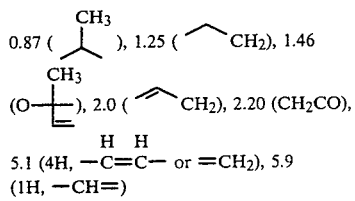

Elementary analysis: Calculated for $C_{38}H_{72}O_2$: C, 81.36; H, 12.94(%). Found: C, 81.51; H, 12.87(%).

EXAMPLE 4

Phytyl decaprenylacetate

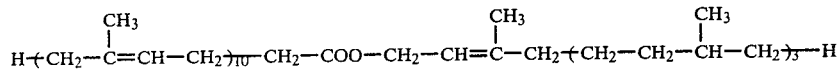

Sodium metal (0.23 g) was dissolved in 100 ml of absolute ethanol. Decaprenylacetic acid (6.1 g) was added to the solution and, after stirring for some time, the ethanol was evaporated under reduced pressure. To a dispersion of the resulting residue in 80 ml of dry benzene, 5 ml of oxalyl chloride was added over about 15 minutes under ice cooling and with stirring. The mixture was further stirred overnight. The reaction mixture was concentrated under reduced pressure and was added with 100 ml of dry ethylene chloride. The soluble fraction was added dropwise over about 15 minutes to an ice-cooled and stirred solution of 2.9 g of phytol in 50 ml of dry ethylene chloride and 3 ml of pyridine, and the mixture was further stirred for 3 hours at room temperature. The reaction mixture was poured into 100 ml of stirred ice water and extracted with ether. The ether extract was sequentially washed with water, 5% hydrochloric acid, saturated sodium bicarbonate solution and saturated sodium chloride solution, and then ether was evaporated off under reduced pressure. The residue was purified by silica gel column chromatography to give 5.2 g of phytyl decaprenylacetate as colourless oil.

IR$\nu_{max}$ cm$^{-1}$: 1740 (C=O), 1660 (C=C).
NMR $\delta_{TMS}^{CDCl_3}$:

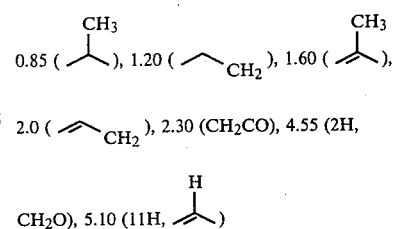

Elementary analysis: Calculated for $C_{72}H_{122}O_2$: C, 84.80; H, 12,06(%). Found: C, 84.96; H, 12.21(%).

The following compounds were prepared in an analogous manner. The results of infrared absorption (IR) and elementary analysis of those compounds are shown in Table 5, and that of nuclear magnetic resonance (NMR) spectrum measurements in Table 6.

Table 5

| Compound No. | Compounds | IR (cm$^{-1}$) $\nu$C = C | IR (cm$^{-1}$) $\nu$C = C. | Calculated C | Calculated H | Found C | Found H | C,H,O |
|---|---|---|---|---|---|---|---|---|
| 8 | Phytyl geranylacetate | 1730 | 1670 | 80.93 | 12.31 | 80.94 | 12.16 | $C_{32}H_{58}O_2$ |
| 9 | Phytyl citronellylacetate | " | " | 80.61 | 12.68 | 80.88 | 12.29 | $C_{32}H_{60}O_2$ |
| 10 | Phytyl farnsylacetate | " | " | 80.85 | 12.25 | 80.96 | 12.76 | $C_{37}H_{66}O_2$ |
| 11 | Phytyl phytylacetate | " | " | 81.75 | 13.07 | 82.12 | 13.24 | $C_{42}H_{80}O_2$ |
| 12 | Phytyl laurate | " | " | 80.26 | 13.05 | 80.23 | 13.11 | $C_{32}H_{62}O_2$ |
| 13 | Phytyl palmitate | " | " | 80.83 | 13.19 | 80.74 | 13.06 | $C_{36}H_{70}O_2$ |
| 14 | Phytyl stearate | " | " | 81.07 | 13.25 | 81.38 | 13.02 | $C_{38}H_{79}O_2$ |

Table 5-continued

| Compound No. | Compounds | IR (cm$^{-1}$) $\nu C=C$ | IR (cm$^{-1}$) $\nu C=C$. | Elementary analysis (%) Calculated C | Calculated H | Found C | Found H | C,H,O |
|---|---|---|---|---|---|---|---|---|
| 15 | Phytyl elaidate | " | " | 81.36 | 12.94 | 81.42 | 13.15 | $C_{38}H_{72}O_2$ |
| 16 | Phytyl linoleate | " | " | 81.65 | 12.62 | 81.63 | 12.47 | $C_{38}H_{77}O_2$ |
| 17 | Phytyl petroselinate | " | " | 81.36 | 12.94 | 81.41 | 12.91 | $C_{38}H_{72}O_2$ |
| 18 | Phytyl ricinoleate | " | " | 79.10 | 12.58 | 78.70 | 12.23 | $C_{38}H_{72}O_3$ |
| 19 | Phytyl 9,10-exoxystearate | " | " | 79.10 | 12.58 | 79.19 | 12.64 | $C_{38}H_{72}O_3$ |
| 20 | Phytyl erucate | " | " | 81.75 | 13.07 | 81.69 | 12.91 | $C_{42}H_{80}O_2$ |
| 21 | Phytyl brassidate | " | " | 81.75 | 13.07 | 81.84 | 12.95 | $C_{42}H_{80}O_2$ |
| 22 | Dihydrophytyl stearate | 1740 | — | 80.78 | 13.56 | 80.91 | 13.58 | $C_{38}H_{76}O_2$ |
| 23 | Dihydrophytyl oleate | 1740 | — | 81.07 | 13.25 | 81.22 | 13.36 | $C_{38}H_{74}O_2$ |

TABLE 6

$\delta$ values (CDCl$_3$ solution, TMS, 60 MHz)

| Compound No. | CH$_3$ ⟨⟩ | ⟨⟩CH$_2$ | CH$_3$ ⟨⟩ | ⟨⟩CH$_2$ / CH$_2$ | CH$_2$CO | CH$_2$O | H ⟨⟩ | Remarks |
|---|---|---|---|---|---|---|---|---|
| 8 | 0.85 | 1.20 | 1.60, 1.68 | 1.95 | 2.20 | 4.44 (2H) | 5.10 (3H) | |
| 9 | " | " | 1.60, 1.70 | 1.90 | " | 4.45 (2H) | 5.10 (2H) | |
| 10 | " | 1.30 | 1.60, 1.70 | 1.95 | " | 4.50 (2H) | 5.10 (4H) | |
| 11 | " | " | 1.67 | 1.90 | " | 4.50 (2H) | 5.10 (2H) | |
| 12 | " | 1.25 | 1.70 | 1.95 | " | 4.57 (2H) | 5.30 (1H) | |
| 13 | " | " | " | " | 2.20 | 4.53 (2H) | 5.20 (1H) | |
| 14 | " | 1.30 | " | " | " | 4.57 (2H) | 5.30 (1H) | |
| 15 | 0.87 | 1.23 | 1.67 | " | " | 4.45 (2H) | 5.27 (3H) | |
| 16 | 0.85 | 1.25 | 1.68 | " | " | 4.55 (2H) | 5.35 (5H) | 2.75(2H, ⟨⟩CH$_2$⟨⟩) |
| 17 | " | " | 1.65 | " | 2.30 | 4.53 (2H) | 5.20 (3H) | |
| 18 | " | 1.30 | " | " | 2.20 | 4.55 (2H) | 5.30 (3H) | 3.5 (1H, —CH—OH) |
| 19 | " | " | 1.70 | " | 2.30 | 4.60 (2H) | 5.32 (1H) | 2.90(2H, —CH—O—CH—) |
| 20 | " | 1.30 | 1.70 | 2.0 | 2.30 | 4.55 (2H) | 5.27 (3H) | |
| 21 | " | 1.25 | 1.68 | 1.95 | " | 4.55 (2H) | 5.30 (3H) | |
| 22 | " | " | — | — | 2.27 | 4.10 (2H) | — | |
| 23 | " | 1.27 | — | 2.0 | 2.30 | 4.10 (2H) | 5.32 (2H) | |

EXAMPLE 5

Solanesyl oleate

Sodium oleate (6.4 g) was dispersed in 60 ml of dry benzene containing 1 ml of dry pyridine, and 7 ml of oxalyl chloride was added thereto with stirring and under ice-cooling. The mixture was stirred further for 2 hours at room temperature. After concentration under reduced pressure, the reaction mixture was stirred with 80 ml of dry benzene, and then the soluble fraction was added over about 20 minutes to a solution of 15 g of solanesol in 100 ml of dry benzene and 8 ml of dry pyridine under ice cooling and with stirring. The mixture was further stirred for 2 hours at room temperature. The reaction product was poured into 150 ml of stirred ice water, extracted with ether, and the ether extract was sequentially washed with water, dilute hydrochloric acid, saturated sodium bicarbonate solution and saturated sodium chloride solution. The removal of the solvent under reduced pressure and silica gel column chromatography of the residue gave 14.4 g of solanesyl oleate as colourless oil.

IR$\nu_{max}$ cm$^{-1}$: 1730 (C=O), 1670 (C=C).
NMR $\delta_{THS}^{CDCl_3}$:

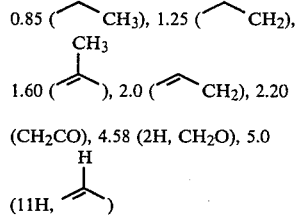

0.85 (⟨⟩CH$_3$), 1.25 (⟨⟩CH$_2$),
1.60 (⟨⟩), 2.0 (⟨⟩CH$_2$), 2.20
(CH$_2$CO), 4.58 (2H, CH$_2$O), 5.0
(11H, ⟨⟩)

Elementary analysis: Calculated for $C_{63}H_{106}O_2$: C, 84.50; H, 11.93(%). Found: C, 84.71; H, 11.95(%).

The following compounds were prepared in an analogous manner. The results of elementary analysis and nuclear magnetic resonance spectrum (NMR) measurements of those compounds are summarized in Table 7 and Table 8 respectively.

Table 7

| Compound No. | Compounds | Empirical formula | Elementary analysis (%) Calculated C | Calculated H | Found C | Found H |
|---|---|---|---|---|---|---|
| 24 | Solanesyl geranylacetate | $C_{57}H_{92}O_2$ | 84.59 | 11.46 | 84.60 | 11.25 |

Table 7-continued

| Compound No. | Compounds | Empirical formula | Elementary analysis (%) Calculated C | H | Found C | H |
|---|---|---|---|---|---|---|
| 25 | Solanesyl farnesylacetate | $C_{62}H_{100}O_2$ | 84.87 | 11.48 | 84.66 | 11.38 |
| 26 | Solanesyl phytylacetate | $C_{67}H_{114}O_2$ | 84.47 | 12.06 | 84.75 | 11.77 |
| 27 | Solanesyl solanesylacetate | $C_{92}H_{148}O_2$ | 85.91 | 11.60 | 86.32 | 11.48 |
| 28 | Solanesyl decaprenylacetate | $C_{97}H_{156}O_2$ | 86.03 | 11.61 | 86.34 | 11.37 |
| 29 | Decaprenyl elaidate | $C_{68}H_{114}O_2$ | 84.75 | 11.92 | 84.91 | 11.99 |
| 30 | Decaprenyl oleate | $C_{68}H_{114}O_2$ | 84.75 | 11.92 | 85.02 | 12.14 |
| 31 | Decaprenyl petroselinate | $C_{68}H_{114}O_2$ | 84.75 | 11.92 | 84.60 | 11.78 |
| 32 | Decaprenyl brassidate | $C_{72}H_{122}O_2$ | 84.80 | 12.06 | 84.95 | 12.33 |
| 33 | Decaprenyl geranylacetate | $C_{62}H_{100}O_2$ | 84.87 | 11.48 | 85.07 | 11.18 |
| 34 | Decaprenyl farnesylacetate | $C_{67}H_{108}O_2$ | 85.10 | 11.51 | 85.42 | 11.54 |
| 35 | Decaprenyl phytylacetate | $C_{72}H_{122}O_2$ | 84.80 | 12.06 | 84.97 | 11.86 |
| 36 | Decaprenyl solanesylacetate | $C_{97}H_{156}O_2$ | 86.03 | 11.61 | 86.02 | 11.47 |
| 37 | Decaprenyl decaprenylacetate | $C_{102}H_{164}O_2$ | 86.11 | 11.62 | 86.47 | 11.75 | the reaction mixture at reduced pressure, 100 ml of dry ethylene chloride was added thereto. The soluble fraction was added over about 15 minutes to a solution of 10.4 g of α-tocopherol dissolved in 100 ml of dry ethylene chloride and 7 ml of dry pyridine, under ice cooling and with stirring. The mixture was further stirred for 2 hours at room temperature. The reaction mixture was poured into 100 ml of stirred ice water and extracted with ether. The ether extract was sequentially washed with water, 5% hydrochloric acid, saturated sodium bicarbonate solution and saturated sodium chloride solution. The removal of the solvent under reduced pressure and silica gel column chromatography of the resulting residue gave 4.8 g of α-tocopheryl solanesylacetate as colourless oil.

IR $\nu_{max}$ cm$^{-1}$: 1760 (C=O), 1670 (C=C).

NMR $\delta_{TMS}^{CDCl_3}$:

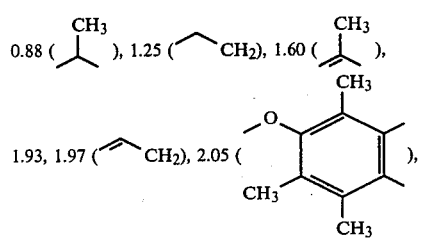

TABLE 8

δ values (CDCl₃ solution, TMS, 60 MHz)

| Compound No. | $\overset{CH_3}{\underset{}{\diagup\!\diagdown}}$ | $\diagup\!\diagdown_{CH_2}$ | $\overset{CH_3}{\underset{}{=}}$ | $\overset{\diagup\!CH_2}{\underset{CH_2}{=}}$ | CH₂CO | CH₂O | $\overset{H}{\diagup\!\diagdown}$ |
|---|---|---|---|---|---|---|---|
| 24 | — | — | 1.60 | 1.97 | 2.30 | 4.50(2H) | 5.05(11H) |
| 25 | — | — | 1.60 | 1.98 | 2.30 | 4.45(2H) | 5.07(12H) |
| 26 | 0.85 | 1.23 | 1.60 | 2.00 | 2.20 | 4.45(2H) | 5.05(10H) |
| 27 | — | — | 1.60 | 1.97 | 2.30 | 4.50(2H) | 5.05(18H) |
| 28 | — | — | 1.60 | 1.98 | 2.30 | 4.45(2H) | 5.05(19H) |
| 29 | 0.85 | 1.25 | 1.58 | 1.97 | 2.25 | 4.45(2H) | 5.03(12H) |
| 30 | 0.85 | 1.30 | 1.65 | 2.05 | 2.20 | 4.60(2H) | 5.14(12H) |
| 31 | 0.87 | 1.30 | 1.60 | 2.00 | 2.30 | 4.55(2H) | 5.05(12H) |
| 32 | 0.85 | 1.30 | 1.60 | 1.95 | 2.20 | 4.50(2H) | 5.10(12H) |
| 33 | — | — | 1.60 | 2.00 | 2.30 | 4.45(2H) | 5.05(12H) |
| 34 | — | — | 1.58 | 1.97 | 2.30 | 4.45(2H) | 5.05(13H) |
| 35 | 0.85 | 1.20 | 1.60 | 1.98 | 2.20 | 4.45(2H) | 5.05(11H) |
| 36 | — | — | 1.60 | 1.97 | 2.30 | 4.50(2H) | 5.05(19H) |
| 37 | — | — | 1.60 | 1.98 | 2.30 | 4.45(2H) | 5.05(20H) |

EXAMPLE 6

α-Tocopheryl solanesylacetate

Solanesylacetic acid (7.4 g) was added to a solution of 0.26 g of sodium metal dissolved in 100 ml of absolute ethanol, and after stirring for some time, the ethanol was evaporated off under reduced pressure. The residue was dispersed in 100 ml of dry benzene. To the dispersion which had been added with 2-3 drops of dry pyridine, 5 ml of oxalyl chloride was added under ice-cooling and with stirring. The mixture was further agitated for 2 hours at room temperature. After concentration of Elementary analysis: Calculated for $C_{76}H_{124}O_3$: C, 84.07; H, 11.51(%). Found: C, 84.28; H, 11.29(%).

The following compounds were prepared in an analogous manner. The results of elementary analysis and nuclear magnetic resonance spectrum measurements of those compounds are summarized in Table 9 and Table 10 respectively.

Table 9

| Compound No. | Compounds | Empirical Formula | Elementary analysis (%) | | | |
|---|---|---|---|---|---|---|
| | | | Calculated | | Found | |
| | | | C | H | C | H |
| 38 | α-Tocopheryl geranylacetate | $C_{41}H_{68}O_3$ | 80.86 | 11.26 | 81.17 | 11.05 |
| 39 | α-Tocopheryl citronellylacetate | $C_{41}H_{70}O_3$ | 80.59 | 11.55 | 80.88 | 11.39 |
| 40 | α-Tocopheryl farnesylacetate | $C_{46}H_{76}O_3$ | 81.60 | 11.31 | 81.53 | 11.14 |
| 41 | α-Tocopheryl phytylacetate | $C_{51}H_{90}O_3$ | 81.54 | 12.08 | 81.80 | 11.89 |
| 42 | α-Tocopheryl decaprenylacetate | $C_{81}H_{130}O_3$ | 84.46 | 11.38 | 84.39 | 11.35 |

TABLE 10

δ values (CDCl₃ solution, TMS, 60 MHz)

| Compound No. | $\underset{CH_3}{\underset{|}{CH_3}}$ | $\text{CH}_2$ | $\underset{CH_3}{\underset{|}{>}}$ | $\underset{CH_2}{\underset{||}{>CH_2}}$ | (aromatic CH₃) | CH₂CO and (aromatic) | $\underset{O}{\underset{|}{CH_2}}$ | H |
|---|---|---|---|---|---|---|---|---|
| 38 | 0.88 | 1.23 | 1.60, 1.67 | 1.90, 1.93 | 2.05 | 2.50 | | 5.10(2H) |
| 39 | " | 1.25 | 1.60, 1.67 | 1.90, 1.95 | " | " | | 5.05(1H) |
| 40 | " | " | 1.60, 1.67 | 1.90, 1.95 | " | " | | 5.10(3H) |
| 41 | " | " | 1.68 | 1.90, 1.95 | 2.07 | " | | 5.15(1H) |
| 42 | " | " | 1.60 | 1.97 | 2.05 | " | | 5.05(10H) |

EXAMPLE 7

Saturated decaprenol

Decaprenol (26 g) was dissolved in 300 ml of ethanol. A suspension of 1.5 g of Raney-Ni (W-1) in 10 ml of ethanol was added thereto, and hydrogenation was performed in an autoclave at 80° C. for 10 hours with shaking under 90 kg/cm² of hydrogen. The catalyst was filtered off and the filtrate was concentrated. The residue weighing 26 g was purified by means of silica gel column chromatography to give 7.2 g of saturated decaprenol, the physical constants of which are given below.

IR$\nu_{max}$ cm⁻¹: 3350 (—OH).

NMR $\delta_{TMS}^{CDCl_3}$: 3.70 (CH₂O), 1.20 (CH₂) 0.85 (CH₃).

Elementary analysis: Calculated for $C_{50}H_{102}O$: H, 14.29; C, 83.48(%). Found: H, 14.23; C, 83.38(%).

EXAMPLE 8

Preparation of dihydrophytol

Phytol (30.0 g, 0.101 mol) was dissolved in 200 ml of ethanol. A suspension of 1.8 g of Raney-Ni (W-1) in 5 ml of ethanol was added thereto, and hydrogenation was carried out under hydrogen for about 5 hours so that 2405 ml of hydrogen (theoretical volume at 24° C.; 2465 ml) was absorbed. After filtering off the catalyst through a filter paper, the ethanol was evaporated. Yield 29.9 g. Silica gel column chromatography with benzene-hexane (1:1) gave 24.7 g of the title compound (yield 82.3%).

Preparation 1

Hard capsules

Solanesylacetic acid (25 g) and 7.5 g of polyoxyethylene-castor oil were dissolved in acetone and then 25 g of anhydrous silicic acid was added. After evaporating the acetone off, the resulting product was mixed with 5 g of carboxymethylcellulose calcium, 5 g of corn starch, 7.5 g of hydroxypropylcellulose and 20 g of microcrystalline cellulose ("Avicel"), and the whole was kneaded with the addition of 30 ml of water. The product was made into granules through a pelletizer equipped with a No. 24 mesh screen (B.S.) ("Xtruder Twin" ® of Fugi-Paudal Co.). The granules were dried to reduce the water content thereof to less than 5%, and then sieved through a No. 16 mesh screen (B.S.). The granules were then filled into capsules using a filling machine, at the rate of 190 mg per capsule.

Preparation 2

Soft capsules

Methyl decaprenylacetate (50 g) and 130 g of fractionated coconut oil were mixed together to form a homogeneous solution. A gelatin solution consisting of 93 g of gelatin, 19 g of glycerol, 10 g of D-sorbitol, 0.4 g of ethyl p-hydroxybenzoate, 0.2 g of propyl p-hydroxybenzoate and 0.4 g of titanium dioxide was prepared. Using manual punching method, soft capsules each containing 180 mg were prepared from a sheet of said gelatin solution.

Preparation 3

Solution for injection

Isopropyl decaprenylacetate (5 g), a proper quantity of arachis oil and 1 g of benzyl alcohol were mixed together and the whole quantity was made to 100 ml with the addition of additional arachis oil. One milliliter each of the solution was aseptically filled in an ampoule and the ampoule was heat sealed.

Preparation 4

Hard capsules

Phytyl geranylacetate (25 g) and 7.5 g of polyoxyethylene-castor oil were dissolved in acetone and then 25 g of anhydrous silicic acid was added. After evaporating the acetone off, the resulting product was mixed with 5 g of carboxymethylcellulose calcium, 5 g of corn starch, 7.5 g of hydroxypropylcellulose and 20 g of microcrystalline cellulose, and the whole was kneaded with the addition of 30 ml of water. The product was made into granules through a pelletizer equipped with a No. 24 mesh screen (B.S.) ("Xtruder Twin" ® of Fuji-Paudal Co.). The granules were dried to reduce the water content thereof to less than 5% and then sieved through a No. 16 mesh screen (B.S.). The granules were then filled into capsules using a filling machine at the rate of 190 mg per capsule.

Preparation 5

Hard capsules

Solanesyl oleate (25 g) and 7.5 g of polyoxyethylene-castor oil were dissolved in acetone and then 25 g of anhydrous silicic acid was added. After evaporating the acetone off, the resulting product was mixed with 5 g of carboxymethylcellulose calcium, 5 g of corn starch, 7.5 g of hydroxypropylcellulose and 20 g of microcrystalline cellulose, and the whole was kneaded with the addition of 30 ml of water. The product was made into granules through a pelletizer equipped with a No. 24 mesh screen (B.S.) ("Xtruder Twin" ® of Fuji-Paudal Co.). The granules were dried to reduce the water content thereof to less than 5% and then sieved through a No. 16 mesh screen (B.S.). The granules were then filled into capsules using a filling machine at the rate of 190 mg per capsule.

Preparation 6

Soft capsules

Phytyl decaprenylacetate (50 g) and 130 g of fractionated coconut oil were mixed together to form a homogeneous solution. A gelatin solution consisting of 93 g of gelatin, 19 g of glycerol, 10 g of D-sorbitol, 0.4 g of ethyl p-hydroxybenzoate, 0.2 g of propyl p-hydroxybenzoate and 0.4 g of titanium dioxide was prepared. Using this gelatin solution in manual punching method, soft capsules each containing 180 mg were prepared.

Preparation 7

Soft capsules

Decaprenyl phytylacetate (50 g) and 130 g of fractionated coconut oil were mixed together to form a homogeneous solution. A gelatin solution consisting of 93 g of gelatin, 19 g of glycerol, 10 g of D-sorbitol, 0.4 g of ethyl p-hydroxybenzoate, 0.2 g of propyl p-hydroxybenzoate and 0.4 g of titanium dioxide was prepared. Using this gelatin solution in manual punching method, soft capsules each containing 180 mg were prepared.

Preparation 8

Solution for injection

Phytyl oleate (5 g), a proper quantity of arachis oil and 1 g of benzyl alcohol were mixed together and the whole quantity was made to 100 ml with the addition of additional arachis oil. One milliliter each of the solution was aseptically filled in an ampoule and the ampoules were heat sealed.

Preparation 9

Solution for injection

Decaprenyl oleate (5 g), a proper quantity of arachis oil and 1 g of benzyl alcohol were mixed together and the whole quantity was made to 100 ml with the addition of additional arachis oil. One milliliter each of the solution was aseptically filled in and ampoule and the ampoules were heat-sealed.

Preparation 10

Hard capsules

α-Tocopheryl geranylacetate (25 g) and 7.5 g of polyoxyethylene-castor oil were dissolved in acetone and then 25 g of anhydrous silicic acid was mixed in. After evaporating the acetone off, the resulting product was mixed with 5 g of carboxymethylcellulose calcium, 5 g of corn starch, 7.5 g of hydroxypropylcellulose and 20 g of microcrystalline cellulose, and the whole was kneaded with the addition of 30 ml of water. The product was made into granules through a pelletizer equipped with a No. 24 mesh screen (B.S.) ("Xtruder Twin" ® of Fuji-Paudal Co.). The granules were dried to reduce the water content thereof to less than 5% and then sieved through a No. 16 mesh screen (B.S.). The granules were then filled into capsules using a filling machine at the rate of 190 mg per capsule.

Preparation 11

Soft capsules

α-Tocopheryl decaprenyl acetate (50 g) and 130 g of fractionated coconut oil were mixed together to form homogeneous solution. A gelatin solution consisting of 93 g of gelatin, 19 g of glycerol, 10 g of D-sorbitol, 0.4 g of ethyl p-hydroxybenzoate, 0.2 g of propyl p-hydroxybenzoate and 0.4 g of titanium dioxide was prepared. Using this gelatin solution in manual punching method, soft capsules each containing 180 mg were prepared.

Preparation 12

Solution for injection

α-Tocopheryl phytylacetate (5 g), a proper quantity of arachis oil and 1 g of benzyl alcohol were mixed together and the whole quantity was made to 100 ml with the addition of additional arachis oil. One ml each of the solution was aseptically filled in an ampoule and the ampoules were heat sealed.

Preparation 13

Hard capsules

Decaprenol (25 g) and 7.5 g of polyoxy ethylene-castor oil were dissolved in acetone and then 25 g of anhydrous silicic acid was added. After evaporating the acetone off, the resulting product was mixed with 5 g of carboxymethylcellulose calcium, 5 g of corn starch, 7.5 g of hydroxypropylcellulose and 20 g of microcrystalline cellulose, and the whole was kneaded with the addition of 30 ml of water. The product was made into granules through a pelletizer equipped with a No. 24 mesh screen (B.S.) ("Xtruder Twin" ® of Fuji-Paudal Co.). The granules were dried to reduce the water content thereof to less than 5% and then sieved through a No. 16 mesh screen (B.S.). The granules were then filled into capsules using a filling machine at the rate of 190 mg per capsule.

Preparation 14

Soft capsules

Solanesol (50 g) and 130 g of fractionated coconut oil were mixed together to form a homogeneous solution. A gelatin solution consisting of 93 g of gelatin, 19 g of glycerol, 10 g of D-sorbitol, 0.4 g of ethyl p-hydroxybenzoate, 0.2 g of propyl p-hydroxybenzoate and 0.4 g of titanium dioxide was prepared. Using this gelatin solution in manual punching method, soft capsules each containing 180 mg of content were prepared.

Preparation 15

Solution for injection

Saturated decaprenol (5 g), a proper quantity of arachis oil and 1 g of benzyl alcohol were mixed together and the whole quantity was made to 100 ml with the addition of additional arachis oil. One milliliter each of the solution was aseptically filled in an ampoule and the ampoules were heat sealed.

What we claim is:

1. A composition for the treatment of ulcer which comprises, as active ingredient, an antiulcer effective amount of α-tocopheryl derivative selected from the group consisting of α-tocopheryl geranylacetate, α-tocopheryl citronellylacetate, α-tocopheryl farnesylacetate, α-tocopheryl solaneylacetate, α-tocopheryl decaprenylacetate and α-tocopheryl phytylacetate in a pharmaceutically acceptable carrier.

2. An α-tocopheryl derivative selected from the group consisting of α-tocopheryl geranylacetate, α-tocopheryl citronellylacetate, α-tocopheryl farnesylacetate, α-tocopheryl solanesylacetate, α-tocopheryl decaprenylacetate and α-tocopheryl phytylacetate.

* * * * *